United States Patent
Watson (10) Patent No.: US 10,465,511 B2
(45) Date of Patent: Nov. 5, 2019

(54) APPARATUS AND METHODS FOR AUTOMATED DRILLING FLUID ANALYSIS SYSTEM

(71) Applicant: KCAS Drilling, LLC, Weatherford, TX (US)

(72) Inventor: James Kelly Watson, Weatherford, TX (US)

(73) Assignee: KCAS Drilling, LLC, Weatherford, TX (US)

( * ) Notice: Subject to any disclaimer, the term of this patent is extended or adjusted under 35 U.S.C. 154(b) by 62 days.

(21) Appl. No.: 15/637,492

(22) Filed: Jun. 29, 2017

(65) Prior Publication Data

US 2018/0003048 A1  Jan. 4, 2018

Related U.S. Application Data

(60) Provisional application No. 62/356,042, filed on Jun. 29, 2016.

(51) Int. Cl.
*E21B 49/08* (2006.01)
*G01N 33/28* (2006.01)
(Continued)

(52) U.S. Cl.
CPC ............ *E21B 49/088* (2013.01); *E21B 21/01* (2013.01); *G01N 33/2823* (2013.01); *G06F 16/00* (2019.01); *E21B 47/00* (2013.01)

(58) Field of Classification Search
CPC ... E21B 49/08; E21B 21/06; G01N 35/00584; G01N 35/00; G01N 33/2823; G01N 2035/0439
See application file for complete search history.

(56) References Cited

U.S. PATENT DOCUMENTS 4,441,561 A  4/1984  Garmong
4,557,142 A  12/1985  Hensley et al.
(Continued)

OTHER PUBLICATIONS

Global Drilling Fluids & Chemicals, Ltd.; Global Insta Labs; Portable Mud Labs; 1 page; website; www.oil-drilling-fluids.com/k2/portable-mud-labs; copyright oil-drilling-fluids.com; undated webpage downloaded May 31, 2016.
(Continued)

*Primary Examiner* — David J Bagnell
*Assistant Examiner* — Dany E Akakpo
(74) *Attorney, Agent, or Firm* — Whitaker Chalk Swindle & Schwartz PLLC; Stephen Mosher (57) ABSTRACT

A mobile apparatus supported on a trailer measures, analyzes, and monitors drilling fluids on an oil & gas site. The system includes a modular automated test unit having instruments for measuring and analyzing physical and chemical drilling fluid parameters including but not limited to viscosity, density, pH, electrical stability, fluid loss, rheological parameters, retort analysis, titrations for mF, pF, POM, chlorides, hardness, calcium, and chromatographic analysis. The system further includes a manifold system situated between a drilling mud reservoir and a network of conduits, for distributing drilling fluid to be analyzed by the instruments. Also included is a system hub, coupled as an interface between a program-operated data processing and communication system and the manifold and system instruments, for communicating control and data information and routing storage in a database of the data outputs of the instruments.

13 Claims, 7 Drawing Sheets

(51) Int. Cl.
*G06F 17/30* (2006.01)
*E21B 47/00* (2012.01)
*G06F 16/00* (2019.01)
*E21B 21/01* (2006.01)

(56) References Cited

U.S. PATENT DOCUMENTS

| | | |
|---|---|---|
| 6,105,415 A | 8/2000 | Kenney |
| 8,191,416 B2 | 6/2012 | Kuchuk et al. |
| 8,973,660 B2 | 3/2015 | DiFoggio |
| 8,981,957 B2 | 3/2015 | Gano et al. |
| 9,038,725 B2 | 5/2015 | Daussin |
| 2009/0032446 A1 | 2/2009 | Weimers et al. |
| 2011/0005765 A1* | 1/2011 | Cumming ............... E21B 41/04 166/344 |
| 2011/0257887 A1* | 10/2011 | Cooper ............... E21B 47/1015 702/12 |
| 2015/0268374 A1* | 9/2015 | Rapoport ................ E21B 49/08 702/6 |
| 2015/0316527 A1 | 11/2015 | Stock et al. |

OTHER PUBLICATIONS

MudlabsTechnology; Mud Performance Monitoring; 3 pages; copyright 2016; article; mudlabs.com/services/article-10/.

\* cited by examiner

APPARATUS AND METHODS FOR AUTOMATED DRILLING FLUID ANALYSIS SYSTEM

CROSS REFERENCE TO RELATED APPLICATIONS

The present application claims priority to U.S. Patent Application Ser. No. 62/356,042 entitled APPARATUS AND METHODS FOR AUTOMATED ON SITE COMPOSITION, ADMINISTRATION, AND ANALYSIS OF DRILLING FLUIDS and filed Jun. 29, 2016 by the same inventor.

BACKGROUND OF THE INVENTION

1. Field of the Invention

The present invention generally relates to the management of drilling fluid uses at an oil & gas drilling site, and more particularly to a system, apparatus, and methods for automated analysis of drilling fluids at a drilling site.

2. Description of the Invention and Background of the Prior Art

The process of drilling oil and gas wells typically includes the use of various compositions of drilling fluids to facilitate the process. Some of the purposes of drilling fluids or muds include but are not limited to remove cuttings of rock and other debris from the formation, to operate downhole tools using the power of hydraulic fluid, to control drilling parameters and cool and lubricate the drill bit, to control erosion in the borehole, to stabilize the formation, etc. Other purposes include controlling formation pressures, and to control substances embodied in the fluids encountered in the formation. Various chemicals, in liquid, solid, or gas form may be combined with water (aqueous-based) or mineral oil (non-aqueous-based) to meet specific needs of the drilling site.

Drilling fluids are designed to embody a variety of properties depending on the particular needs of the drilling operation. These properties include weight and density, viscosity, chemical composition, pH, and hardness. In addition, rheological measurements are often needed to measure the flow characteristics of the drilling mud such as shear stress arising from the flow velocity and viscosity of the fluid within the well. Often it is necessary to know whether the fluid is liquid or a mixture of liquid and solids, or of liquid and gas, which are known respectively in the art as continuous, dis-continuous, and gas phases of the drilling fluid. Thus in general it is necessary to continually analyze and monitor the composition and parameters of the drilling fluids to ensure that they are functioning as designed.

Facilities for measuring drilling fluids vary widely, and traditional services, which typically must be staffed by a mud technician or engineer, very often produce results of limited comprehensiveness, accuracy, or use. There are many and varied reasons that drilling fluid measurement and monitoring systems presently available fail to perform to optimum levels. Errors in calibration of the equipment and or transcription of results are commonplace. Safety is sometimes compromised by inattentiveness of operators or other personnel tasked with performing the required tests. Wasteful use of additives and other products to the fluid impairs cost efficiency. Tests run by inexperienced or unqualified personnel can negate the utility of results. The availability of test data is often not very timely or is subject to the judgment of the service provider.

What is needed is an accurate, reliable, comprehensive system for measuring and monitoring drilling fluids that operates automatically, requires minimal attention after set up, and produces regular and timely reports of drilling fluid performance to rig operators so that the uses of drilling fluids may be optimized.

SUMMARY OF THE INVENTION

A mobile, automated drilling fluid analysis system that continuously performs analysis tests in sequence and periodically at timed intervals, and stores the data in a database, is provided, comprising a housing disposed on a mobile frame and configured for connections to electrical power, and a fluid conduit system from and to a drilling fluid reservoir; a computer system disposed within the housing and configured with non-volatile storage, a communications interface to a network, and a suite of program software for controlling operations of the analysis system to measure, analyze, store, communicate, and compose output displays, summaries, and reports thereof through graphical peripherals and remote connections to the system; an automated test unit enclosed within the housing and coupled through a manifold to the fluid conduits system, the automated test unit having a dual, motor-driven turntable including a first turntable for measuring physical parameters and a second turntable for measuring chemical parameters; and a metering mechanism for depositing drilling fluid samples pumped through the fluid conduits from the drilling fluid reservoir into test containers on the first or second turntables; wherein the automated test unit provides for receiving, sensing, and measuring multiple physical and chemical parameters of the drilling fluid samples in a prescribed, continuous sequence according to analysis routines of the program software and compiling the analyzed parameters for storage or display.

In one aspect the modular automated test unit may be constructed as a self-contained unit configured for operating in several alternative modes depending on the particular combination of tests the ADFA system 10 is set up to perform. As noted previously, the system may be configured to operate unattended, continuously according to a predetermined sequence of tests.

In another aspect, the operating program applications comprise program sequences for controlling individual electric actuators to regulate the flow of fluid to and from each instrument; receiving and storing raw data in the system database; compiling data outputs provided from the instruments; sending the compiled data from the system database via wireless link to one or more external terminals on request; and organizing the timing and sequence of measurement and analysis operations on samples of drilling fluid distributed from the manifold according to information about the type of drilling fluid.

In another aspect, the plurality of instruments comprises an assembly of instruments for measuring and analyzing viscosity, density, pH, electrical stability, fluid loss, rheological parameters, retort analysis, titrations for mF, pF, POM, chlorides, hardness, calcium, and chromatographic analysis.

DETAILED DESCRIPTION OF THE INVENTION

In an advance in the state of the art the present invention provides a comprehensive computer controlled laboratory analysis system contained in a mobile housing or trailer. The system includes all of the computer processing and measurement analysis instrumentation needed to measure all properties of interest of various types of drilling fluids (aka, drilling mud) in use at active oil & gas drilling sites. The system performs the measurements, receives, compiles, and stores the data, prepares reports, and responds to requests to upload the data to external terminals both to on-site and to remote office locations. The system fully automates the tasks of taking samples of the drilling fluid pumped through the system, performs physical and chemical measurement and analysis on the samples continuously or according to a predetermined schedule, reports the data, and monitors the condition of drilling fluid at the site of the drilling operations.

The principle benefits of the system include the ability to provide measurements and analysis of all necessary drilling fluid parameters, a substantially improved accuracy of the measurements, reducing or eliminating the need for an on-site technician or engineer to perform the tests and prepare reports of the analyses, reporting the data on a continuous or periodic basis, and the ability to upload results responsive to requests from external locations. All of these advantages together provide increased productivity of the drilling operations.

For example, precision measurements of mud weight, viscosity, density, whether liquids or slurries, can be measured by mass flowmeters coupled to the system. Accurate rheological measurements may be made using viscometers that automatically heat the sample fluid for measurement instead of using a simple thermometer to determine when the specified temperature of the sample is reached. The automated system described herein can create complete, API standardized drilling fluid reports at user-specified intervals and transmit them to mud and drilling engineers, who may be remotely located, and to rig operating personnel in the dog house according to the rig owner or operator's requirements. Calibrations of the system instruments can be carried out automatically and periodically to ensure accuracy. When the system to be described herein is understood, persons skilled in the art will realize the versatility of the concept, that a variety of instrumentation may be incorporated into the system.

The system is mobile and thus can be towed to the customer's site, connected to the mud reservoir, and set up and calibrated with minimal downtime or interruption of rig functions. The system replaces the traditional limited monitoring facilities requiring a staff member's presence with a self-contained machine that provides periodic and comprehensive reports essentially in real time.

A key and novel part of the mobile, automated drilling fluid analysis system described herein is a modular automated test unit for computer-controlled testing of both solid and fluid constituents of drilling fluid in a single device or test unit. This device includes first and second rotatable test container platforms (aka "turntables") that are driven by a common drive shaft coupled to an electric motor. The first platform is in an upper portion of the test unit and the second platform is in a lower portion of the test unit. This upper platform may be provided in two or more interchangeable versions, depending on the suite of tests that must be performed. In the illustrated examples, there are two types of platforms used in the upper portion of the test unit, type A configured for filtration and filter cake tests, and type B configured for solids and fluid percentage tests.

The second rotating platform of the modular automated test unit structure, which may be termed a type C platform, is located in a lower portion of the test unit device. This platform tests the filtrate and determines density and constituent percentage measurements, whether the filtrate is water based mud (WBM) or oil-based mud (OBM). For example, it can test whether the oil based mud in use contains water, a condition that should be documented. The density is tested by subjecting the filtrate to two different "floats" that have weights that correspond to the densities of water based and oil based drilling fluids ("muds"). DI (deionized) water alone has a density of 8.334 pounds per gallon (ppg). Oil alone may have a density between 6.7 to 7.5 ppg. Thus, a 5.0 ppg float will float on water or oil. A 8.3 ppg float will not float on water alone but may float on a mixture of water and oil. The use of the floats in the filtrate tests will be described herein below.

The platforms or turntables in the upper portion of the modular automated test unit are filled by an automated titration system (aka "automated loader"). The test tubes in the lower rotating platform are filled by a vacuum pump and condenser system that receives drilling fluid from the outlet of the upper platform. A first version of the first or upper platform (type A) may be used for filtering the drilling fluid, testing fluid loss and filter cake of a drilling fluid sample titrated into a cup. The first platform, when alternately configured with beakers (type B), may also be used for testing solids and fluid percentage of a sample titrated into a beaker. The platforms are circular and contain a plurality of positions for holding the cups or beakers so that they may be rotated from one indexed position to another to test a series of samples, for example at timed intervals.

The second rotatable test platform (type C) in the lower portion of the automated test unit, also circular, has a similar number of positions for test tubes containing samples of the fluid transferred from the first platform through the vacuum pump and condenser system disposed within the automated test unit. The tests performed by the second test platform may be called "chemical" tests, in contrast with the tests performed by the first platform, which may be called "physical" tests.

There are at least two possible configurations of the modular automated test unit. A first configuration is to house interchangeable upper test platforms (either type A and B) and a lower test platform (type C) in a single housing. In this case the modular automated test unit may be operable in two modes—mode I and mode II—as will be described. In a second configuration, two separate automated test units may be each housed in a separate housing, one dedicated to mode I and the other dedicated to mode II. The entire system may be configured in a variety of ways without departing from the concept of a fully automated drilling mud analysis system assembled from the components to be described herein.

This modular automated test unit is an important part of the entire system that will be described herein, as shown in block diagram form in FIG. 4. The entire system is capable of performing a comprehensive series of tests on drilling fluid on a continuous schedule. The schedule may include repetition of certain tests. The sequence of tests described herein may, for example, include funnel viscosity and density tests, an electric stability meter, and an in line rheometer, followed by the automated test unit for testing fluid loss, filter cake, solids and fluid percentage, etc. For convenience and portability, the system is self-contained and housed in a trailer that may be towed from location to location, connected to a source of electrical power and a drilling mud pit or reservoir, and set up for unattended operation with a minimum of time and attention to calibration, etc. The system includes interface devices for communication with remote offices or other facilities.

The entire system, including the modular automated test unit module, is programmed for computer control to perform at least the following kinds of operations, in addition to the operation of each of the instruments in the system: (1) controlling individual valve actuators via a system manifold and a system hub or interface to regulate the flow of fluid to and from each instrument through a system of conduits coupled to the manifold; (2) activating sensors and other measurement devices to take samples; (3) compiling data outputs provided from the instruments; (4) receiving and storing raw data in a database both on-site and at a remote office; (5) sending the compiled data from the database via wireless link to one or more external terminals on request; and (6) organizing the timing and sequence of measurement and analysis operations on samples of drilling fluid distributed from the manifold according to information about the type of drilling fluid.

The following detailed description of an exemplary embodiment, is illustrated in the accompanying drawings to depict and explain the concepts and operation of the present invention. Reference numbers appearing on more than one figure refer to the same structural feature.

Figure 1:
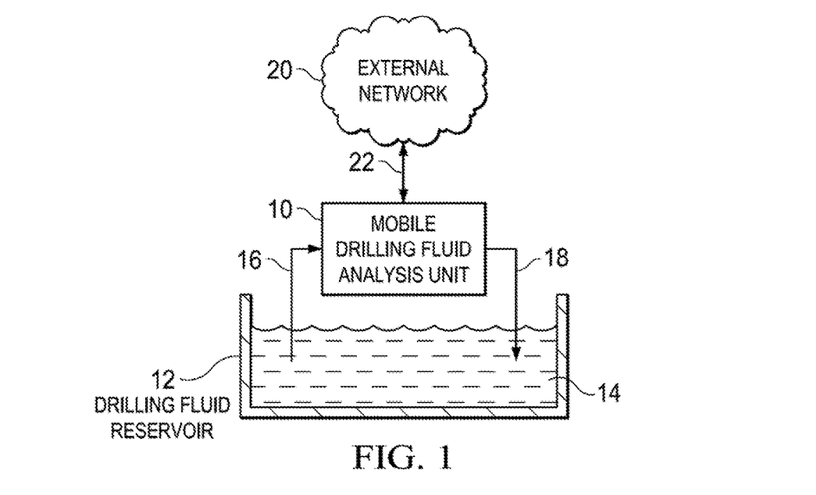
FIG. 1 illustrates a system block diagram of the present invention according to one embodiment.

FIG. 1 illustrates a system block diagram of the present invention according to one embodiment. The mobile, automated drilling fluid analysis system ("ADFA") 10 is connected between a drilling fluid reservoir 12 on an oil or gas drilling site and an external network 20 for communicating with a remote office or terminal (not shown). The reservoir 12 contains drilling fluid or mud 14 deposited after use during drilling a well. The drilling mud 14 is retained for reuse. The ADFA 10 is used for analyzing samples drawn through conduit 16 to determine various physical and chemical properties of the drilling mud. Fluid is returned to the reservoir 12 after analysis through the conduit 18.

Figure 2:
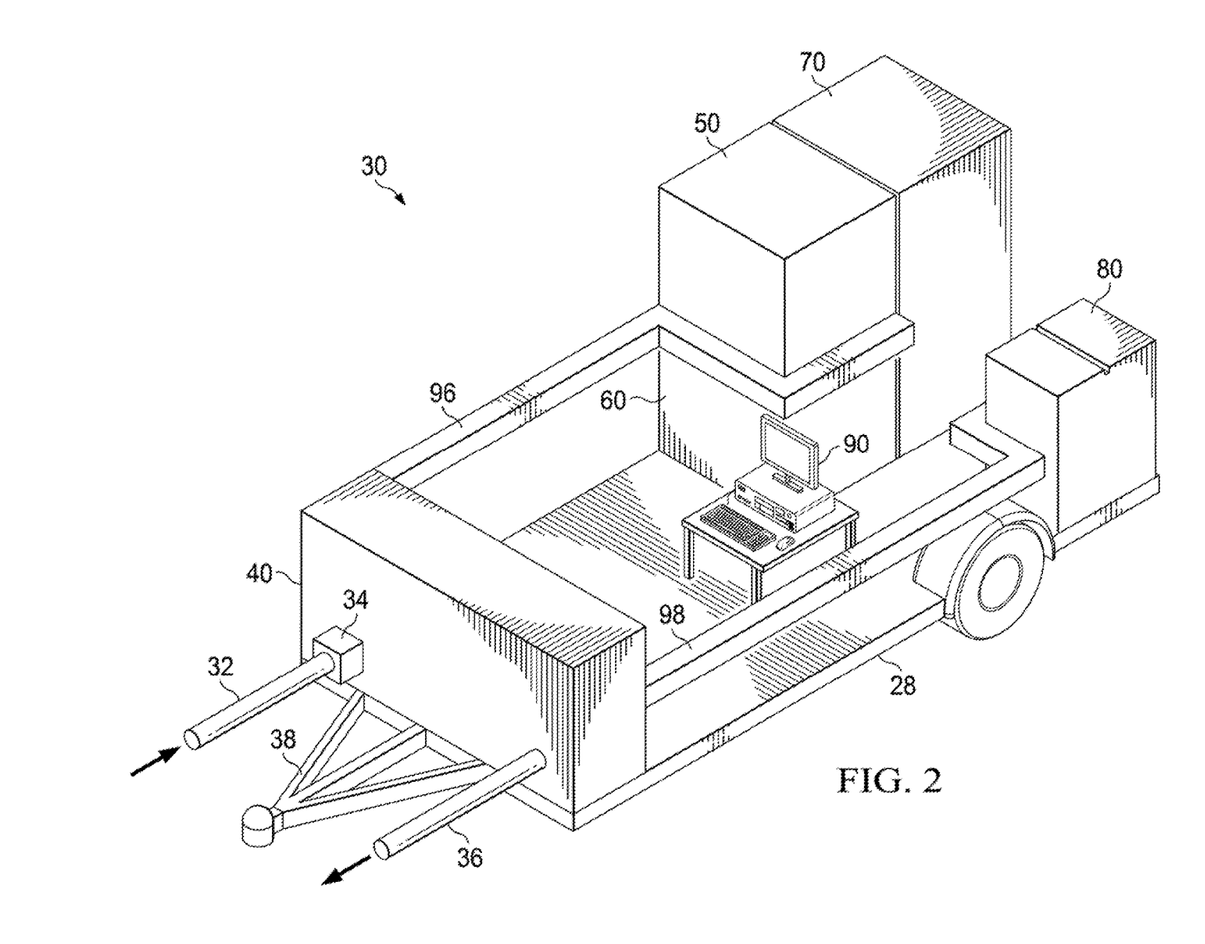
FIG. 2 illustrates a pictorial drawing of a mobile automated drilling fluid analysis system installed on a trailer chassis and including its operative components, according to the one embodiment of FIG. 1

FIG. 2 illustrates a pictorial drawing of a mobile, automated drilling fluid analysis system 30 installed on a trailer chassis 28 and including its operative components, according to the one embodiment. The trailer 28 may include a trailer hitch frame assembly 38 for towing the trailer from place to place or maneuvering it into position at a site of use. A trailer body to enclose the equipment is not shown to more clearly depict its contents. The diagram illustrates the relationships of the individual components with one another. However, their actual physical locations may vary according to a particular embodiment. A fluid line 32 from the reservoir 12 supplies drilling fluid 14 via a pump 34 to a manifold system that may be located within a cabinet 40 on the trailer 28. The manifold system, a ubiquitous device well understood in the art, is contained within the cabinet 40. The manifold system, which has an inlet coupled the fluid line 32 and a plurality of actuator-controlled outlets to individual instruments, functions as a kind of distribution hub between the active pits and the various instruments of the system.

A fluid line 36 provides a return path from the automated drilling fluid analysis system 10, located generally on the trailer 28, to the reservoir 12. The fluid may be circulated through the system by a main pump 34 and by auxiliary pumps (not shown) operated by actuators (not shown) controlled by the workstation 90 or by a server operating by remote control.

The instruments, including the modular automated test unit, may generally be housed in cabinets within the trailer 28. In the illustrated example, a first cabinet 50, supplied fluid for analysis by conduit 96, may contain a first automated test unit (or first ATU), not shown but may be located inside cabinet 50, for example. The first ATU, configured for Mode I analysis, may preferably include an automatic titrator for feeding fluid samples to first and second rotating turntables respectively. The Mode I analysis includes tests for filter cake using the first turntable and tests for fluid loss using the second turntable as will be described with FIG. 5. A second ATU, perhaps contained in a second cabinet 60 in this example and supplied fluid for analysis by the conduit 96, may be configured for Mode II analysis. In Mode II the ATU may also preferably include an automatic titrator for feeding fluid samples to first and second rotating turntables respectively. The Mode II analysis includes tests for the solid content of the drilling fluid using the first turntable and tests for fluid percentages using the second turntable as will be described with FIG. 6.

The trailer 28 may be configured for including a variety of other drilling fluid analysis instruments. For example, a third cabinet 70 may be used for housing a chromatography unit (not shown) and conduits and actuators for controlling the movement of drilling fluids inlet via conduit 98 to the instrument. Similarly, a fourth cabinet 80 may be used for housing viscometer rheometers (not shown) or other instruments supplied drilling fluid for testing by automatic titrators (not shown). These components not shown are similar in general function to the instruments to be described in detail that are depicted in FIGS. 4, 5 and 6 herein. Return paths for drilling fluids following the analysis tests performed within the cabinets 50, 60, 70, and 80 may be provided through the conduits 96 and 98. A workstation 90 such as a desktop computer (not visible in FIG. 1) for use by an operator, such as for set up, or attended operation, etc., may be installed in a separate cabinet on the trailer 30 or on a small table within the body of the trailer 28.

Figure 3:
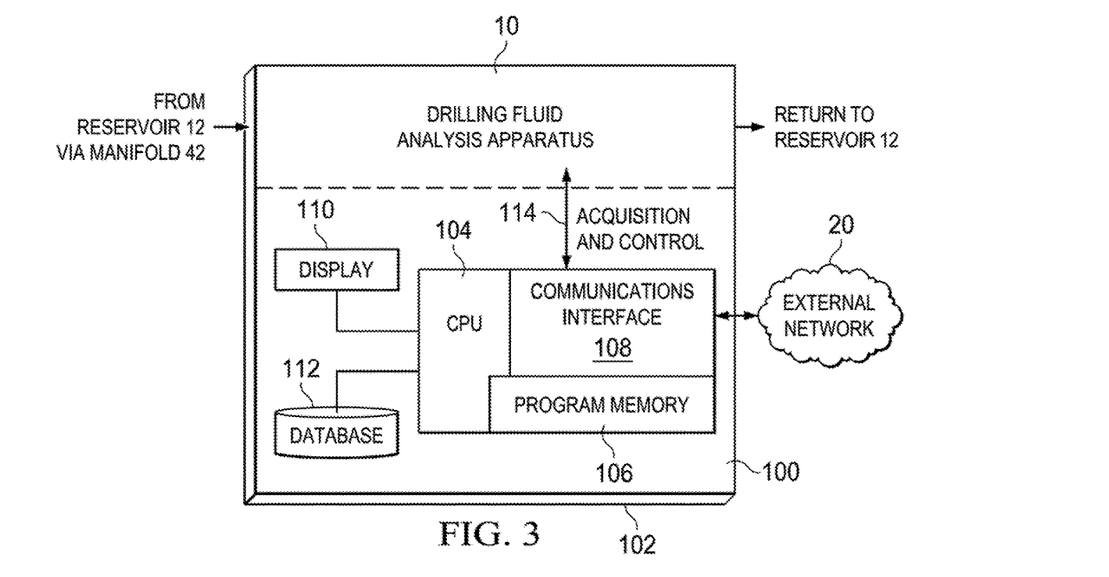
FIG. 3 illustrates a block diagram depicting the data processing and communications system operatively connected to the automated drilling fluid analysis system of FIGS. 1 and 2.

FIG. 3 illustrates a block diagram depicting the data processing and communications system operatively connected to the automated drilling fluid analysis system of FIGS. 1 and 2. The automated drilling fluid analysis (ADFA) system 10 and the computer system 100 provided for its programmed control form an integral system 102, although the physical units may be located within different cabinets on the trailer 28. For example, the ADFA 10 may be located in second cabinet 50 while the computer system 100 may be located in the first cabinet 40 with the manifold system. The particular choice is left up to determination by the manufacturer. In the drawing, a CPU 104, includes at least a program memory 106, and a communication interface 108 for connection with an external network 20. The CPU 104 may also be connected to a display 110 and a database 112. The program memory 106 may contain software programs for operating the pumps and valve actuators disposed for controlling the flow of fluids through the instrumentation within the trailer 28 and for communicating with a remote office via the network 20. Communication with the external network 20 may include signals for operating control, revision of testing sequences, reporting results or alarm indications and the like. The database 112 provides storage for test results and for supplying test data upon request. The acquisition and control signals are communicated to the ADFA 10 via the control lines 114.

Figure 4:
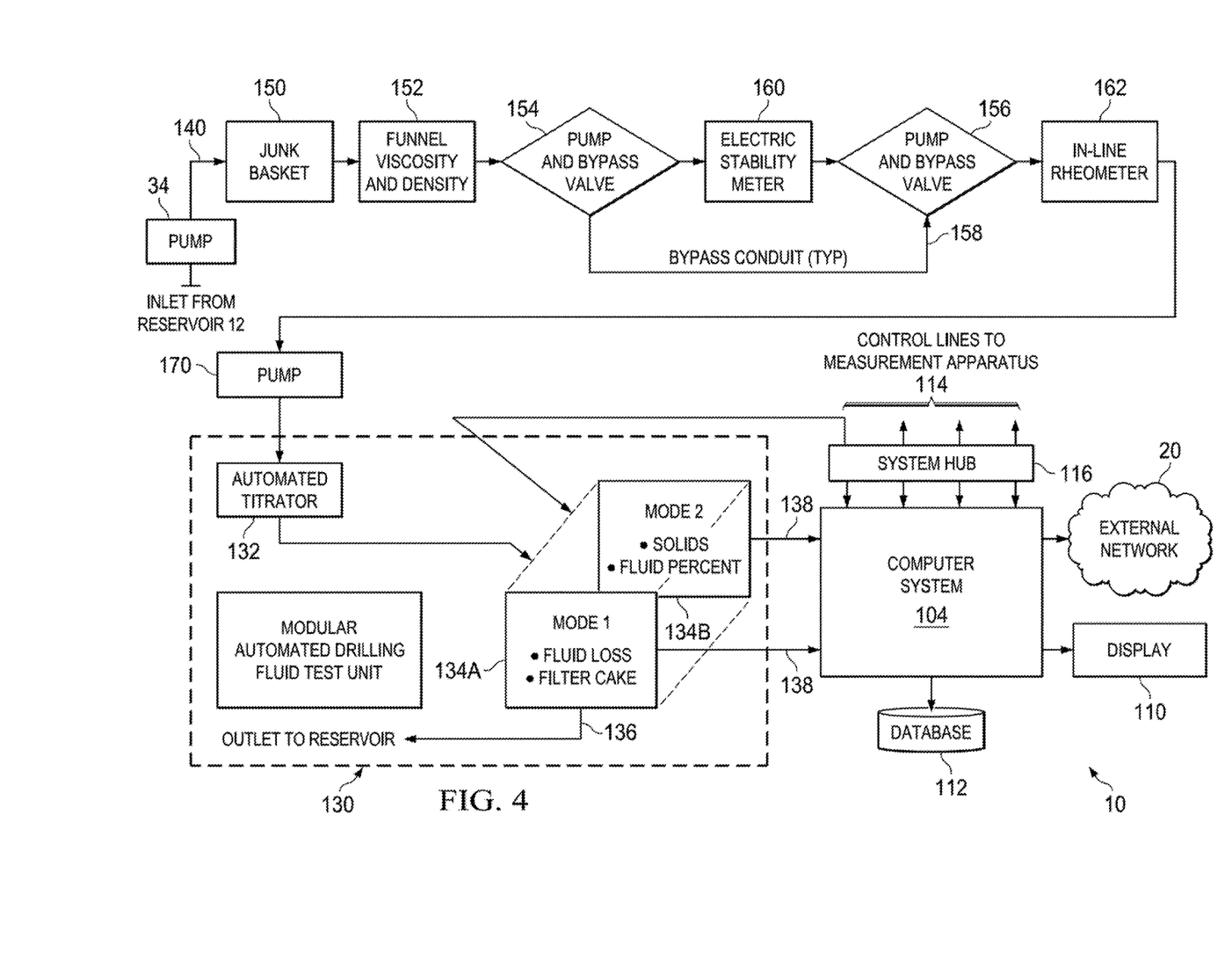
FIG. 4 illustrates a system block diagram with components arranged in a sequence for analyzing drilling fluid according to the embodiment of FIGS. 1, 2 and 3.

FIG. 4 illustrates a system block diagram with components arranged in a sequence for analyzing drilling fluid according to the embodiment of FIGS. 1, 2 and 3. The ADFA 10 may be adapted to include a variety of instrumentation for measuring and analyzing the constituents and properties of drilling fluids. The example shown in FIG. 4 is illustrative but should not be construed as limiting to the particular instruments and components included in the diagram. The Modular automated drilling fluid test unit 130 (also identified as "automated test unit" elsewhere in this description) is a new and novel component, designed specifically for this application because of the lack of any other currently available system with its capabilities. The test unit 130 combines facilities not previously available in a self-contained unit for testing and monitoring both physical and chemical properties automatically and continuously according to a predetermined sequence and schedule. This capability provides substantial operating efficiencies that result from the automated control, lack of need for an attendant to operate the system, record the data, change the sequence, initialize the equipment before each round of tests, etc. The result is a significant advance in the state of the art, providing improved accuracy of test data as well as reducing the need for—and the expense of—on-site personnel to operate the system.

The entry point of the exemplary system 10 begins at the inlet from the drilling fluid reservoir 12. Fluid is pumped from the reservoir by main pump 34 through a conduit 140 and a "junk basket" 150 to remove material that is likely to clog the instrumentation or contaminate the measurements. Several conventional instruments such as a funnel viscosity and density device 152, an electric stability meter 160, and an in-line rheometer 162, all of which are well known in the art may be included within the system 10. A second pump 170 may be used between the outlet of the in-line rheometer and the automated titrator 132 of the modular automated drilling fluid ("ADF) test unit 130. Each of these individual test components may be connected in a bypass loop if it necessary to temporarily bypass a selected test unit because of malfunction, the need for service, or to bypass attest that is not required. The bypass configuration around the electric stability meter, for example, is provided by a pump and bypass valve 154 that routes the test fluid via a conduit 156 to a second pump and bypass valve 158. Both bypass valves 154, 158 may be computer controlled via actuators provided with each valve. The same scheme may be used to bypass other components of the system.

The modular ADF test unit 130 will be described in two versions, a type A as shown in FIG. 5 and a type B as shown in FIG. 6. Type A operates Mode I, designated by reference number 134A. The Mode I (134A) test unit includes tests for fluid loss and filter cake, to be described in FIG. 5. Type B operates Mode II, reference number 134B. The Mode II (134B) test unit includes tests for solids and percentage fluids, to be described in FIG. 6. Both type A and B versions use an automated titrator 132 to supply drilling fluid samples to the respective test fluid containers in the modular ADF test unit 130. Fluids for which tests are completed are sent to the reservoir 12 via a conduit 136. The outputs of the modular ADF test unit 130 are transmitted to the computer system 104 for processing and storage, preparation of reports, communicating results and other information via the network 20 to a remote office or location. The computer system 104 may be connected to a display 110 and a database 112, and also to the various instruments and components via cable 114 containing control and data lines for controlling the Modes I and II test units 134A and 134B and receiving data from the ADFA 10.

The computer system 104, which may comprise a workstation such as a desktop computer configured with operating program software and communications and database components, may also be coupled through a system hub 116 to the manifold system. The system hub 116 functions as an active interface between the computer system 104 that is controlled by comprehensive software and the hardware elements of the system. While the system hub 116 may be coupled to an on-site database, it may also be linked through the communications system to external databases or offices. FIG. 4 thus includes the data control lines for controlling the instruments through actuators connected to the fluid lines. Persons skilled in the art will recognize that the data lines shown may actually resemble a system bus through which both control data and instrument data may be routed.

As noted previously, the system hub 116 functions as an interface between the computer system 104 and the instruments depicted in FIG. 4. Thus, the combination of the computer system 104 and the system hub 116 comprise the main control section of the system 10. The communications interface 108 operates with external elements to enable remote operation, control, and analysis. In most cases, an on-site mud engineer or technician is not required because the system is highly automated by software control. The architecture of the system permits a wide variety of measurement instruments to be controlled by the system. The instruments may be selected from devices specifically designed for high-accuracy measurements.

Figure 5A:
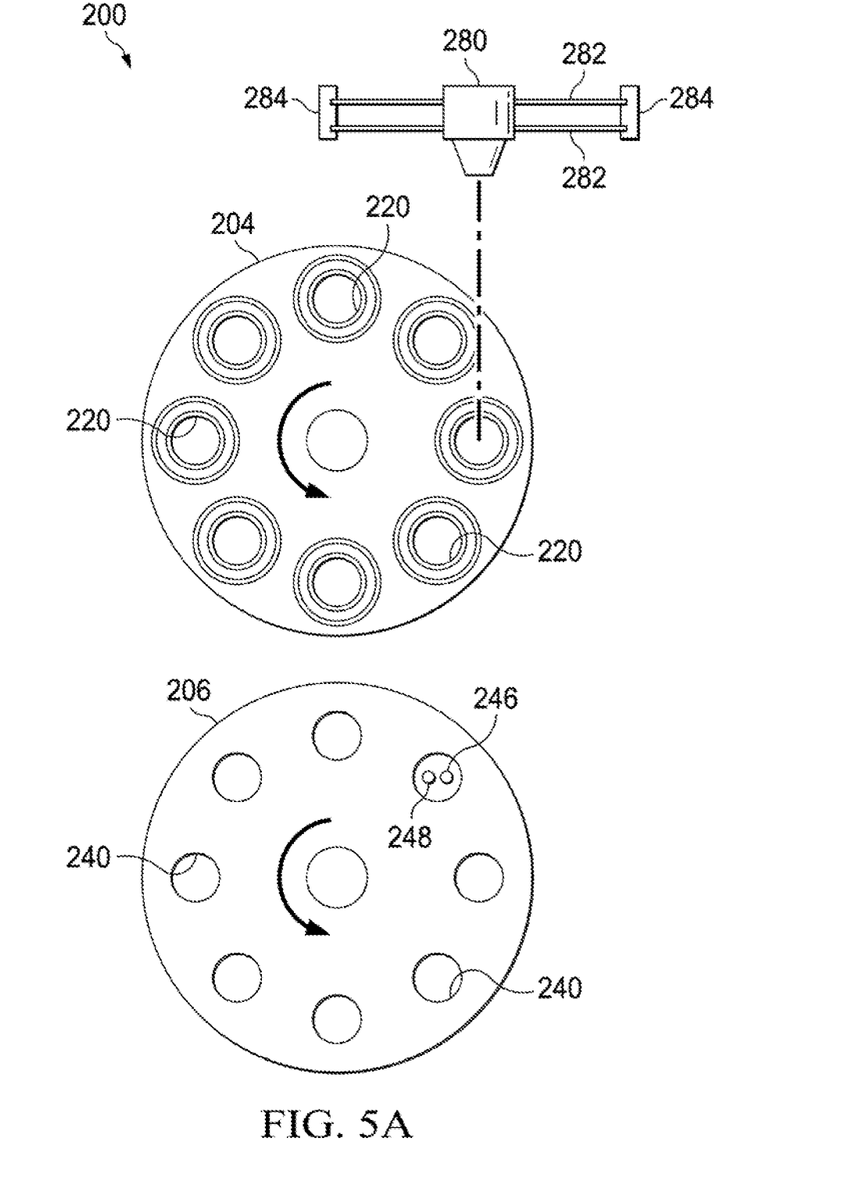
FIG. 5A illustrates a plan view of first and third portions of the modular automated test unit of FIG. 4 configured for a first mode of operation according to one embodiment of the invention.
Figure 5B:
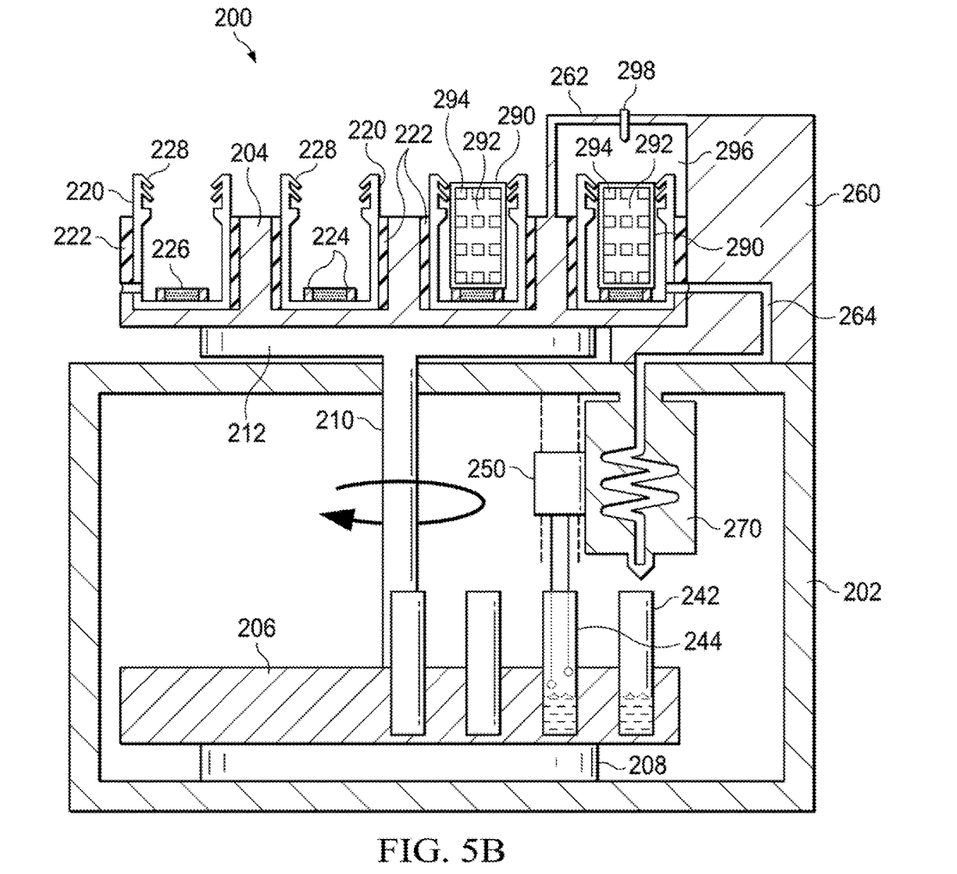
FIG. 5B illustrates a side elevation view of a second (intermediate) portion of the modular automated test unit of FIG. 4 configured for a first mode of operation according to the embodiment of FIG. 5A.

FIGS. 5A and 5B together illustrate a pictorial diagram of a first version, type A of the modular automated test unit 130 of FIG. 4 configured for a first mode—Mode I—of operation according to one embodiment of the invention. This embodiment will be identified by reference number 200 in FIGS. 5A and 5B, which is essentially the same unit referenced by number 134A. The components of test unit 200 may preferably be contained in a single housing 202. The test unit 200 includes first and second rotating turntables 204 and 206 that are coupled to a common drive shaft 210 driven by a motor (not shown) within a base 208 in the lower part of the housing 202. The common shaft 210 is connected to a sub-base 212 at its upper end. The first (upper) rotating turntable 204 is supported by the sub-base 212. The first rotating turntable 204 includes positions for eight test sample cups 220 equally spaced around the perimeter of the turntable 204. The second rotating turntable 206 includes positions for eight test tubes 240 for fluid samples equally spaced around the perimeter of the turntable 206.

Continuing with FIGS. 5A and 5B, a vacuum pump 260 mounted on the housing 202 withdraws fluid samples from the sample cups 220 through a passage 264 and routes it through a condenser 270 to be deposited into a test tube 242 positioned just below the condenser 270. A gas jet 262 provides for blowing CO2/N2 into the test sample cup 220 placed in position below the gas jet 262. This burst of gas is provided during Mode I to facilitate pressurizing the sample after it is heated to a predetermined temperature and before the test sample cup 220 is sealed and pressurized for testing. A density float sensor 250, suspended within the housing 202 just above a test tube 244, inserts first 246 and second 248 density floats into the test tube 244 to gage the density of the drilling fluid sample. Float 246 has a density of 5.0 ppg and float 248 has a density of 8.3 ppg. Drilling fluid samples are supplied to the test sample cups 220 in the first turntable 204 by an automated titrator 280 that may be positioned above the test sample cup 220 along rails supported by brackets 284 of the test unit 200. The titrator 280 may be operated by a solenoid or other device (not shown) under control by the computer 104.

The first rotating turntable 204 of FIGS. 5A and 5B includes features for heating, insulating, spinning, and sealing a sample cup 220 after a sample container 290 is installed and a drilling fluid sample is deposited in the sample container 290. The sample container 290 preferably includes squares of a filtration paper 294 placed within the sample container 290 and retained by clips or slots (not shown) provided for that purpose. The sample container 290 has walls with openings 292 arranged in a grid pattern to permit filtrate to pass from the sample container 290 when the test sample cup 220 is spun during testing. The test sample cups 220 are supported in the rotating turntable 204 in one of eight positions disposed around the perimeter of the turntable. The test sample cups 220 are each surrounded by insulation 222. In the lower part of each sample cup 220 is a heating element 224 surrounding a driven magnet 226. Surrounding the upper rim inside each sample cup 220 are one or more flexible rotary shaft seals for sealing the space within the sample cup 220 and the outside of the sample container 290 when it is installed within the sample cup 220. The driven magnet 226 that is caused to spin by a motor mechanism (not shown). The motor may have a drive magnet 227 similar to the drive magnet 226 but attached to an output shaft so that spinning the drive magnet 227 causes the driven magnet 226 to rotate by the interacting magnetic fields as is well understood by persons skilled in the art. Alternatively, the output shaft of the motor may be attached to the driven magnet 226, either directly or through a gear reduction assembly.

Referring to FIGS. 5A and 5B, the modular automated drilling fluid analysis unit 200 operates in Mode I as follows to perform the following tests: (1) filtration; (2) fluid test; (3) filter cake; (4) density; and (5) volume.

Initializing the apparatus proceeds according to the following steps: (A) install a pre-sized filter paper element (for example, two squares of Whatman® #50 filter paper) into two sides of each test cup 290 of the first turntable 204 using the retaining clips or slots in the test cups, and load the prepared test cups 290 into the test cup chambers 220 disposed around the periphery of the rotating turntable 204, making sure the periphery seals 228 are correctly sealing the test cups. (B) Install clean test tubes 240 into the receptacles of the second turntable 206. (C) Enter the time and date, along with other data such as type of fluid, start time, operating temperature (typically 120 degrees for water based mud; 150 degrees for oil based mud), rotation speed, length of test, test volume, etc. on the workstation 90 or on a control pad (not shown) that may be coupled to the ADFA unit 200.

(D) Initiate filling of the test cups by the automated titrator 280 (or by hand if necessary). (E) Advance the turntable to align the test cup with the vacuum pump station 260 for heating the fluid to the preset temperature, followed by (F) "blow down" of the CO2/N2. Then, (G) pressurize the test cup up to 250 psi (pounds per square inch") and (H) spin the test cup at a predetermined speed between 0 and 200 rpm. This completes the filtering step to produce the filtrate that leads to measuring the thickness of the filter cake deposited on the filter paper during the spinning operation.

(I) Route the fluid after filtering through the vacuum pump 260 and the condenser 270 (to cool the fluid) and into the test tube to measure the density (J) and the volume (K) of fluid and solids in the second rotating turntable 206. (L) When the tests on a test cup are completed, advance the turntables in the ADFA unit 200 to the next test position and repeat the sequence. The density (J) is measured in the test tube 244 that is supported below a density sensor 250. Test tube 244 contains a 5.0 ppg float and a 8.3 ppg float, and the lift or position of the floats is sensed by the density sensor 250. The sensor data for the density and depth in the test tube is analyzed by the computer 104 to convert the density measurements to proportions of water and oil in the density fluid to enable the calculation of the volume of the fluids and solids in the drilling fluid sample. When all tests are completed, the ADFA unit 200 is reset to a neutral condition in readiness for the next testing cycle.

Figure 6A:
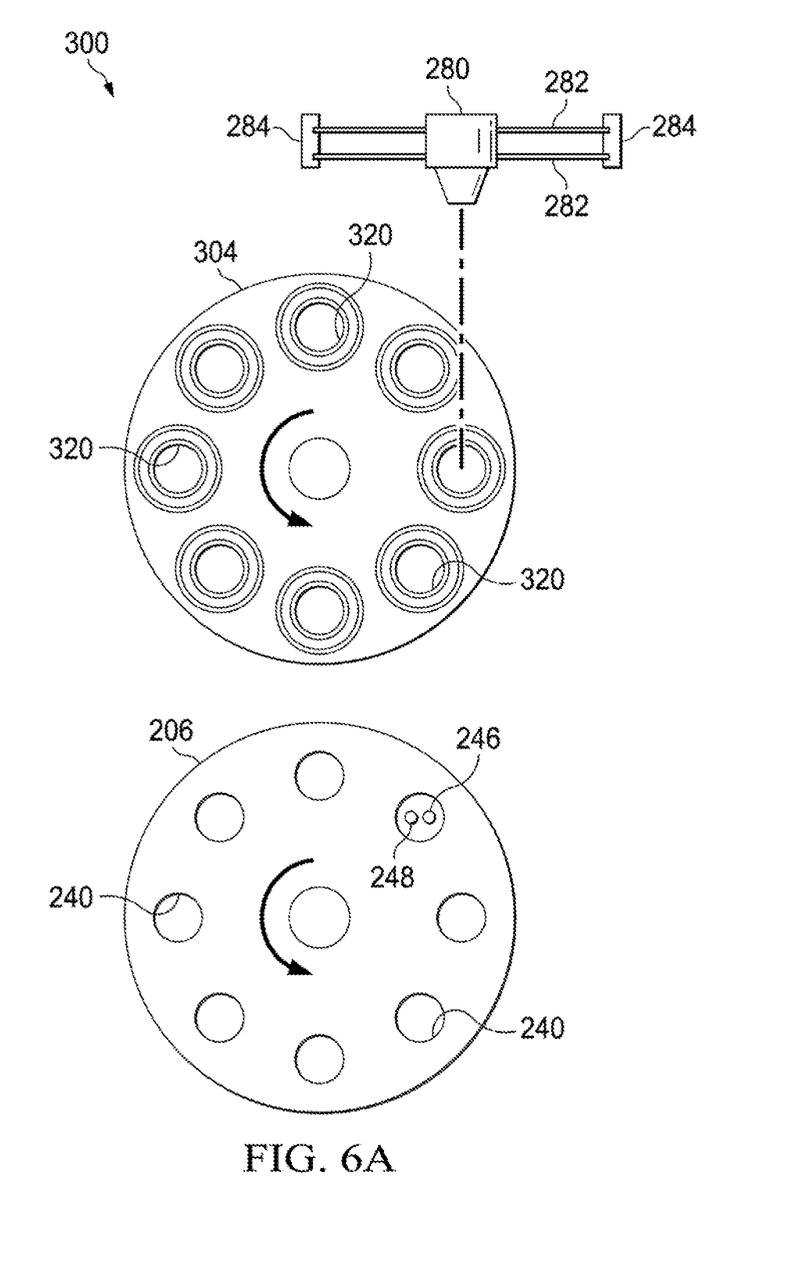
FIG. 6A illustrates a plan vie of first and third of portions of the modular automated test unit of FIG. 4 configured for a second mode of operation according to another embodiment of the invention.
Figure 6B:
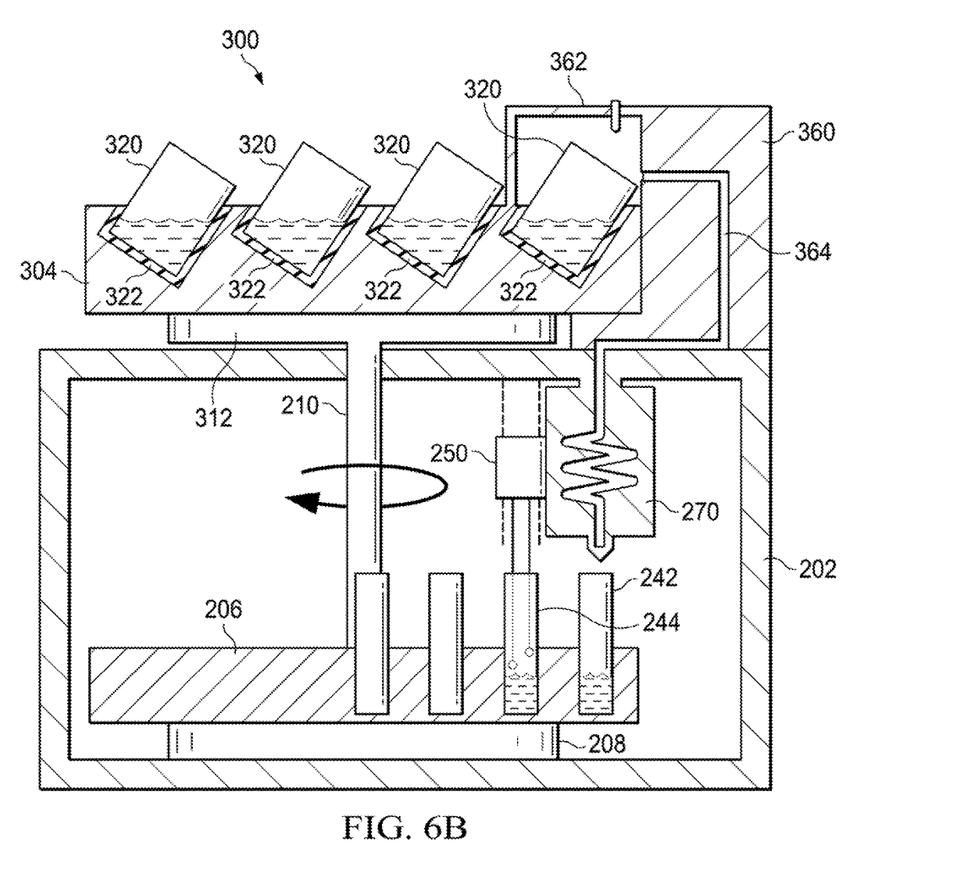
FIG. 6B illustrates a side elevation view of a second (intermediate) portion of the modular automated test unit of FIG. 4 configured for the second mode of operation according to the embodiment of FIG. 6A.

FIGS. 6A and 6B together illustrate a pictorial diagram of a second version, type B of the modular automated test unit 130 of FIG. 4 configured for a second mode—Mode II—of operation according to one embodiment of the invention. This embodiment will be identified by reference number 300 in FIG. 6, which is essentially the same unit referenced by number 134B. The components of test unit 300 may preferably be contained in a single housing 202. The test unit 300 includes first and second rotating turntables 304 and 306 that are coupled to a common drive shaft 210 driven by a motor (not shown) within a base 208 I the lower part of the housing 302. The common shaft 210 is connected to a sub-base 312 at its upper end. The first (upper) rotating turntable 304 is supported by the sub-base 312. The first rotating turntable 304 includes positions for eight test sample cups 320 equally spaced around the perimeter of the turntable 304. The second rotating turntable 206 includes positions for eight test tubes 240 for fluid samples equally spaced around the perimeter of the turntable 206.

Continuing with FIGS. 6A and 6B, a vacuum pump 360 mounted on the housing 202 withdraws fluid samples from the sample cups 320 through a passage 364 and routes it through a condenser 270 to be deposited into a test tube 242 positioned just below the condenser 270. A gas conduit 362 provides for blowing $CO_2/N_2$ over the test sample cup 320 placed in position below the gas jet 362. This burst of gas is provided during Mode II to facilitate evaporation of the air near the surface of the fluid sample after it is heated to a predetermined temperature and before the test sample cup 320 is evacuated for testing. A density float sensor 250, suspended within the housing 202 just above a test tube 244, inserts first 246 and second 248 density floats into the test tube 244 to gage the density of the drilling fluid sample. Float 246 has a density of 5.0 ppg and float 248 has a density of 8.3 ppg. Drilling fluid samples are supplied to the test sample cups 220 in the first turntable 204 by an automated titrator 280 that may be positioned above the test sample cup 320 along rails 282 supported by brackets 284 of the test unit 200. The titrator 280 may be operated by a solenoid or other device (not shown) under control by the computer 104.

The first rotating turntable 304 of FIGS. 6A and 6B includes features for determining the volume amount of water, oil, and solids in the drilling fluid sample deposited in the beaker 320. Each beaker 320, preferably made of stainless steel, is supported at an angle—preferably approximately 55 degrees from vertical—to maximize the surface area of the drilling fluid exposed to a vacuum for increasing evaporation of the drilling fluid. The test sample cups 220 are supported in the rotating turntable 204 in one of eight positions disposed around the perimeter of the turntable. Each sample beaker 320 is surrounded by insulation 322 to minimize the effects of ambient temperatures on the sample drilling fluid. The sample fluid beaker is advanced into position to be enclosed within a test chamber (not shown for clarity), which can be evacuated by a vacuum pump 360. The evaporation process can be facilitated or sped up by introducing $CO_2/N_2$ "blown down" via a gas conduit 362. Following the evaporation steps, the evaporated drilling fluid is withdrawn by the vacuum pump 360 through passage 364 and into the condenser 270 to be cooled before depositing it into a test tube 240.

Referring to FIGS. 6A and 6B, the modular automated drilling fluid analysis unit 300 operates in Mode II as follows to perform the following tests: (1) volume of water, (2) volume of oil; and (3) volume amount of solids. These tests are used to determine the percentages of fluids in the drilling fluid (mud) sample. The set up and initialization procedures are similar to the procedure for the Mode I operation depicted in FIGS. 5A and 5B.

Initializing the apparatus proceeds according to the following steps: (A) install a stainless steel beaker 320 into each angled chamber disposed around the periphery of the rotating turntable 304. (B) Install clean test tubes 240 into the receptacles of the second turntable 206. (C) Enter the time and date, along with other data such as type of fluid, start time, operating temperature (typically 120 degrees for water based mud; 150 degrees for oil based mud), rotation speed, length of test, test volume, etc. on the workstation 90 or on a control pad (not shown) that may be coupled to the ADFA unit 200.

(D) Initiate filling of the test beakers 320 by the automated titrator 280 (or by hand if necessary). (E) Advance the turntable to align the test beaker 320 with the vacuum pump station 260 for heating the fluid to the preset temperature, followed by (F) "blow down" of the CO2/N2. Then, (G) allow the evaporation to occur while (H) subjecting the sample in the beaker 320 to a vacuum to reduce the pressure.

(I) Route the evaporated fluid through the vacuum pump 260 and the condenser 270 (to cool the fluid) and into the test tube to measure the density (J) and the volume (K) of fluid and solids in the second rotating turntable 206. (L) When the tests on a test sample are completed, advance the turntables in the ADFA unit 200 to the next test position and repeat the sequence. The density (J) is measured in the test tube 244 that is supported below a density sensor 250. Test tube 244 contains a 5.0 ppg float and a 8.3 ppg float, and the lift or position of the floats is sensed by the density sensor 250. The sensor data for the density and depth of fluid in the test tube 244 is analyzed by the computer 104 to convert the density measurements to proportions of water and oil in the density fluid to enable calculation of the volumes of fluids and solids in the drilling fluid sample. When all tests are completed, the ADFA unit 200 is reset to a neutral condition in readiness for the next testing cycle.

The foregoing description, read in reference to the accompanying drawings discloses a mobile, automated drilling fluid analysis system that continuously performs analysis tests in sequence and periodically at timed intervals, and stores the data in a database, comprising a housing disposed on a mobile frame that is configured for connections to electrical power, and a fluid conduit system from and to a drilling fluid reservoir. A computer system disposed within the housing and configured with non-volatile storage, a communications interface to a network, and a suite of program software for controlling operations of the analysis system is included to measure, analyze, store, communicate, and compose output displays, summaries, and reports thereof through graphical peripherals and remote connections to the system. The system further includes a modular automated test unit enclosed within the housing and coupled through a manifold to the fluid conduits system, the automated test unit having a dual, motor-driven turntable including a first turntable for measuring physical parameters and a second turntable for measuring chemical parameters. The automated test unit also includes a metering mechanism for depositing drilling fluid samples pumped through the fluid conduits from the drilling fluid reservoir into test containers on the first or second turntables; wherein the automated test unit provides for receiving, sensing, and measuring multiple physical and chemical parameters of the drilling fluid samples in a prescribed, continuous sequence according to analysis routines of the program software and compiling the analyzed parameters for storage or display.

In one aspect the modular automated test unit may be constructed as a self-contained unit configured for operating in several alternative modes depending on the particular combination of tests the ADFA system 10 is set up to perform. As noted previously, the system may be configured to operate unattended, continuously according to a predetermined sequence of tests.

While the invention has been shown in only one of its forms, it is not thus limited but is susceptible to various changes and modifications without departing from the spirit thereof.

What is claimed is:

1. A mobile, automated drilling fluid analysis system that continuously performs analysis tests in sequence and periodically at timed intervals, and stores the data in a system database, comprising:
    a housing disposed on a mobile frame and configured for connections to electrical power, and with a fluid conduit system from and to a drilling fluid reservoir;
    a computer system disposed within the housing and configured with non-volatile storage, a communications interface to an external network, and a suite of program software for controlling operations of the analysis system to measure, analyze, store, communicate, and compose output displays, summaries, and reports thereof through graphical peripherals and remote connections to the fluid analysis system;
    an automated test unit enclosed within the housing and coupled through a manifold to the fluid conduit system, the automated test unit having a dual, motor-driven turntable including a first turntable for measuring physical parameters and a second turntable for measuring chemical parameters; and a metering mechanism for depositing drilling fluid samples pumped through the fluid conduit system from the drilling fluid reservoir into test containers on the first or second turntables; wherein the automated test unit provides for receiving, sensing, and measuring multiple physical and chemical parameters of the drilling fluid samples in a prescribed, continuous sequence according to analysis routines of the program software and compiling the multiple physical and chemical parameters for storage or display.

2. The system of claim 1, further comprising:

a frame within the housing for supporting the automated test unit including the first and second turntables, a motor, the metering mechanism, and a pump system for receiving drilling fluid from the reservoir to be deposited into the test containers.

3. The system of claim 1, wherein the manifold comprises:

a manifold system equipped with valves and valve actuators controlled via control lines from the computer system for distributing the drilling fluid from the reservoir to the automated test unit; and a pump system connected with the fluid conduit system and disposed within the housing with the metering mechanism.

4. The system of claim 3, wherein the pump system comprises:

first and second variable speed pumps for respectively controlling a volume of drilling fluid to the manifold and returning the drilling fluid to the reservoir following analysis in the automated test unit.

5. The system of claim 4, wherein:

the first variable speed pump operates on a first timed interval and the second variable speed pump operates on a second timed interval.

6. The system of claim 1, further comprising:

a plurality of test sensors and instruments disposed within the automated test unit for measuring the multiple physical and chemical parameters; and a data processing hub for connecting between the computer system and a plurality of control points corresponding to the plurality of test sensors and instruments in the automated drilling fluid analysis system.

7. The system of claim 1, further comprising:

the communications interface in the computer system configured for coupling via the external network to a remote computer system for controlling the fluid analysis system, storing measurement data acquired by the remote computer system, and transmitting measurement data to a remote location.

8. The system of claim 1, wherein the automated test unit comprises:

a plurality of instruments for measuring and analyzing drilling fluids, connected to the manifold via the fluid conduit system, wherein access to the instruments is controlled by respective valves and valve actuators.

9. The system of claim 8, wherein the plurality of instruments comprises:

an assembly of instruments for measuring and analyzing viscosity, density, electrical stability, fluid loss, rheological parameters, pH, retort analysis, titrations for mF, pF, POM, chlorides, sulfides, hardness, calcium, and chromatographic analysis.

10. The system of claim 8, wherein the computer system comprises:

a processor having both random access and non-volatile program and data storage memory;

a plurality of data input and data control lines operatively coupled to the processor;

the communication interface coupled to the processor and configured for wired and wireless communication transmission and reception with the external network and with a system hub;

at least one data entry peripheral and at least one data output printing or display peripheral; and the system database for storage of measurement data from the plurality of instruments.

11. The system of claim 10, wherein the system hub comprises:

an intra-system network for facilitating transfer of data and control information between the processor, the automated test unit, the manifold and valve actuators, and the external network.

12. The system of claim 1, wherein the suite of program software comprises program sequences for:

controlling individual valve actuators to regulate the flow of fluid to and from the automated test unit;

organizing the timing and sequence of measurement and analysis operations on samples of drilling fluid distributed from the manifold according to information about the type of drilling fluid;

compiling data outputs into the system database provided from instruments in the automated test unit; and sending the compiled data from the system database via a wireless link to one or more external terminals on request.

13. The system of claim 1, further comprising:

a wheeled trailer for transporting the housing disposed on the mobile frame.

* * * * *